(12) United States Patent
Stockert

(10) Patent No.: US 9,103,730 B2
(45) Date of Patent: Aug. 11, 2015

(54) TEMPERATURE SENSOR FOR MEASUREMENT ON OR IN A LIVING BODY

(76) Inventor: Ruediger Stockert, Freiburg (DE)

( * ) Notice: Subject to any disclaimer, the term of this patent is extended or adjusted under 35 U.S.C. 154(b) by 36 days.

(21) Appl. No.: 13/382,974

(22) PCT Filed: Jul. 10, 2009

(86) PCT No.: PCT/EP2009/005012
§ 371 (c)(1),
(2), (4) Date: Jan. 24, 2012

(87) PCT Pub. No.: WO2011/003432
PCT Pub. Date: Jan. 13, 2011

(65) Prior Publication Data
US 2013/0028290 A1 Jan. 31, 2013

(51) Int. Cl.
*G01K 7/00* (2006.01)
*G01K 7/04* (2006.01)
*G01K 13/00* (2006.01)
*A61B 18/16* (2006.01)
*A61B 18/00* (2006.01)

(52) U.S. Cl.
CPC ............... *G01K 7/04* (2013.01); *G01K 13/002* (2013.01); *A61B 18/16* (2013.01); *A61B 2018/00577* (2013.01); *A61B 2018/00589* (2013.01)

(58) Field of Classification Search
CPC ............ G01K 7/02; G01K 1/08; G01N 25/32
See application file for complete search history.

(56) References Cited

U.S. PATENT DOCUMENTS

| 1,715,316 A | 5/1929 | Thwing |
| 5,033,866 A * | 7/1991 | Kehl et al. ..................... 374/179 |
| 5,288,147 A * | 2/1994 | Schaefer et al. ................ 374/10 |
| 6,084,174 A * | 7/2000 | Hedengren et al. ........... 136/201 |
| 2001/0035300 A1* | 11/2001 | Apostolos ..................... 174/255 |
| 2002/0185169 A1* | 12/2002 | Hamamoto et al. .......... 136/224 |
| 2006/0106375 A1* | 5/2006 | Werneth et al. ................. 606/32 |
| 2007/0049919 A1 | 3/2007 | Lee et al. |

(Continued)

FOREIGN PATENT DOCUMENTS

| EP | 1172070 A1 | 1/2002 |
| EP | 1990020 A2 | 11/2008 |
| JP | 05-090646 | 4/1993 |
| JP | 2007-139530 | 6/2007 |
| WO | 2008045869 A2 | 4/2008 |

OTHER PUBLICATIONS

PCT International Search Report for PCT/EP2009/005012, Apr. 27, 2010.

(Continued)

*Primary Examiner* — Lisa Caputo
*Assistant Examiner* — Nasir U Ahmed
(74) *Attorney, Agent, or Firm* — Robert R. Deleault, Esq.; Mesmer & Deleault, PLLC

(57) ABSTRACT

The invention relates to a temperature sensor (24) for measuring the temperature on or in a living body. The temperature sensor (24) includes a plurality of thermocouples arranged distributed on a measurement surface (30) of the sensor (24) and electrically connected to create at least one series circuit, wherein thermojunctions (16, 18) formed by the thermocouples in each series circuit are divided into at least two, and preferably a total of two, spatially separate groups such that in each group when there is a change in temperature the thermojunctions (16, 18) cause an equivalent change in voltage.

11 Claims, 5 Drawing Sheets

(56) References Cited

U.S. PATENT DOCUMENTS

| | | | |
|---|---|---|---|
| 2008/0004658 A1* | 1/2008 | Malecki et al. | 606/213 |
| 2008/0177175 A1* | 7/2008 | Mottola et al. | 600/424 |
| 2008/0195089 A1 | 8/2008 | Thiagalingam et al. | |
| 2008/0300590 A1* | 12/2008 | Horne et al. | 606/35 |
| 2011/0051776 A1* | 3/2011 | Bieberich et al. | 374/163 |

OTHER PUBLICATIONS

English translation of Office Action for JPA No. 2012-518756, mail date Aug. 27, 2013.

English translation of Office Action for Japanese Patent Application No. 2012-518756, mail date May 13, 2014.

* cited by examiner

TEMPERATURE SENSOR FOR MEASUREMENT ON OR IN A LIVING BODY

The invention relates to a temperature sensor for measuring the temperature on or in a living body, especially for use with thermal energy.

When using thermal energy, time and again tissue overheats or there are burns to the skin. Thus during thermosurgery biological tissue is heated by adding treatment energy in order to attain a specific therapeutic purpose by denaturing the treated tissue. During thermosurgery a particular goal is coagulation or ablation of local tissue areas. For instance, arrhythmia or tachycardia in the heart of a human or animal body may be treated by means of thermal surgery. Frequently undesired overheating of the adjacent tissue occurs during such coagulation or ablation on or in the heart (for instance in the esophagus).

Monopolar and bipolar applications are known in high-frequency electric thermal surgery. During both types of treatment, an alternating high-frequency current for treatment is fed into the body via an application electrode that is brought into the immediate vicinity of the tissue area to be treated. In the bipolar method, the electrical circuit is closed using at least one flat counterelectrode that is exteriorly placed on or attached to the skin of the body at a distance from the application electrode. The counterelectrode is also called a neutral electrode, indifferent electrode, or return electrode. The effective electrode surface of the counterelectrode is large compared to that of the application electrode, which is why under normal circumstances (i.e. the electrode has good contact with the skin) the current density on the counterelectrode is low so that there is no reason to worry about carbonization of the skin there.

The situation changes if the counterelectrode partially detaches from the skin. This may occur if the patient moves and/or if sweat forms, especially during a treatment that lasts for several hours. In this case the current density increases sharply in the areas of the counterelectrode that are still in contact with the skin, and this consequently increases the risk of skin carbonization.

Undesired overheating of tissue occurs mostly only at points, i.e. in a relatively small surface area, both in the tissue areas adjacent to the aforesaid ablation or coagulation site (for instance the esophagus) and in areas where the counterelectrode has not detached from the skin. However, known temperature sensors for measurement on or in a living body determine only mean temperature values for a relatively large surface area measurement area or the surroundings of the temperature sensor so that point overheating of tissue cannot be measured with adequate reliability.

To solve the problem of measuring undesired point overheating of tissue it is possible to use a plurality of temperature sensors. The production and control of a temperature sensor with a plurality of temperature sensors is technically complex, however, and commensurately expensive.

The object of the invention is to provide a temperature sensor for measuring the temperature on or in a living body, which sensor reliably measures point overheating of tissues on or in the living body and can be produced with low technical complexity.

To attain this object, the invention provides a temperature sensor for measuring the temperature on or in a living body and that has a plurality of thermocouples arranged in a distributed manner on a measurement surface of the sensor and electrically connected to form at least one series circuit, wherein thermojunctions formed by the thermocouples in each series circuit are divided between at least two, and preferably a total two, spatially separate groups such that in each group when there is a change in temperature the thermojunctions cause an equivalent change in voltage.

The thermocouples may in particular be thermoelements. The inventive temperature sensor permits temperature changes to be detected at each of the thermojunctions. The temperature changes may be increases in temperature or decreases in temperature. Thus at given temperature increases, all thermojunctions of the first group for instance can cause a positive change in voltage and all thermojunctions of the second group can cause a negative change in voltage. Using the series circuit it is also possible to detect point temperature changes (for instance at only one thermojunction), because the temperature sensor supplies a measured value response (and not just a mean measured value) even for a temperature change that is limited locally. By dividing the thermojunctions into two groups it is furthermore possible to detect the area of the measured surface in which the point temperature change occurs.

Numerous arrangments of thermojunctions on the measurement surface of the temperature sensor are possible. An essentially homogeneous distribution of thermojunctions on the measurement surface is advantageous so that point temperature changes are detected with the greatest possible probability. In particular the thermojunctions may be arranged on the measurement surface, at least in part, such that they are disposed at the corner points of regular tiling. Some of the thermojunctions can preferably be disposed on corner points of regular tiling comprising equilateral triangles, rectangles, or regular hexagons. If the measurement surface has a circular cylinder shape, the equilateral triangles, rectangles, or regular hexagons may also be projected onto the surface of the circular cylinder.

Furthermore, each of the thermojunction groups may essentially be disposed on corner points of regular tiling.

The thermocouples preferably have different first and second electrical conductors. Thus the first and second electrical conductors may be different metals, alloys, or semiconductors with different electrical conductivities. For simple production of thermocouples or of the groups, the temperature sensor may have a layer structure with at least a first layer and a second layer, the first electrical conductors being disposed in the first layer and the second electrical conductors being disposed in the second layer and at least some of the thermojunctions extending between the first and the second layers.

The first and second layers are preferably essentially parallel to one another, the thermojunctions extending between the first and the second layers. In particular the thermojunctions may extend essentially perpendicular to the first and second layers. Depending on the manufacturing process used, parts of the first and/or of the second electrical conductors may be disposed in the extension area between the first and second layers. This provides a three-dimensional structure that is easy to produce and that comprises the first and second electrical conductors and the thermojunctions. The layer structure is preferably disposed on a body forming the measurement surface, for instance a hollow body.

In one preferred embodiment, the first conductors are disposed with no overlap in the first layer and the second conductors are disposed with no overlap in the second layer. Because of this, all of the first and second electrical conductors may be produced in one production step each. Furthermore, at least part of an electrically insulating layer may be arranged between the first and second electrical conductors. In this case the electrically insulating layer is arranged in the layer structure between the first and second layers.

In order to make possible a large number or a high density of thermojunctions per unit of surface area, some of the electrical conductors disposed in the first and second layers may overlap one another.

In accordance with one preferred embodiment, the first and second electrical conductors and the thermojunctions are arranged on a flexible circuit board. This simplifies adapting the conductor structure to a pre-specified measurement surface shape. The flexible circuit board may in particular be glued to the measurement surface of the temperature sensor.

For more precise localization of temperature changes, the thermocouples may be electrically connected to create at least two series circuits. Thus the thermojunctions formed by the thermocouples connected in the at least two series circuits may be divided per series circuit into at least two groups separated spatially from one another such that in each group the thermojunctions bring about an equivalent change in voltage when there is a change in temperature. In this manner temperature changes may be detected in at least four spatial areas. Similarly, the accuracy for localizing temperature changes may be increased using additional series circuits.

In order to also be able to determine with great certainty a point temperature change at a site between the two thermojunction groups of the first series circuit, at least one thermojunction from another series circuit may be arranged between at least two thermojunctions connected in electrical series. If, for instance, the thermojunctions for the first group cause a positive change in voltage when there is an increase in temperature, and the thermojunctions for the second group cause a negative change in voltage when there is an increase in temperature, when a point temperature change occurs between the two groups, the two changes in voltage can offset one another so that the temperature sensor does not supply a measured value different from zero despite an increase in temperature. Such point heating may be detected, however, by arranging at least one thermojunction between the two thermojunction groups of the first series cirucit.

In order to make possible a large number or a high density of thermojunctions per unit of surface area, some of the thermocouples from the at least two series circuits may be arranged overlapping one another on the measurement surface. Alternatively, the thermocouples from the at least two series circuits may also be arranged not overlapping one another on the measurement surface.

It is not necessary for all of the thermocouples to be arranged on the measurement surface. Thus at least some thermojunctions from at least one group may be arranged along a straight line and at least some thermojunctions from at least one other group may be arranged on the measurement surface about the straight line. For instance, the measurement surface may have a cylinder shape, especially a circular cylinder, the thermojunctions of the one group being disposed on a straight line extending through the center point of the cylinder and the thermojunctions of the other group being arranged on the surface of the cylinder. Such a longitudinal shape may preferably be used in esophageal sensors.

Users of temperature sensors are accustomed to the temperature sensor supplying an elevated measured value for increases in temperature. As described in the foregoing, however, the inventive temperature sensor may also supply negative measured values when there are increases in temperature. To avoid this problem, the temperature sensor may have an electrical circuit that supplies the absolute value of the measured value. When there are a plurality of series circuits, the electrical circuit may also form absolute values from measured voltages for the plurality of series circuits.

In accordance with one preferred embodiment, the temperature sensor may also have a temperature sensor for measuring a temperature value. In this embodiment, the electrical circuit may be set up to add the (absolute) temperature value measured by the temperature sensor and the absolute value of the measured value so that the user of the temperature sensor is provided a relative increase in temperature with respect to the temperature value measured by the temperature sensor. If the measurement surface is in the shape of a cylinder, the temperature sensor may preferably be arranged inside the measurement surface, the thermocouples being disposed on the measurement surface about the temperature sensor.

The inventive temperature sensor may preferably be used in an esophageal sensor. In accordance with one preferred embodiment, the esophageal sensor has a longitudinal, circular cylinder shape, at least some of the thermocouples being arranged on the surface of the circular cylinder. The length of the esophageal sensor is adapted to the length of the esophagus to be measured. To this end, the esophageal sensor may be embodied as longitudinally modifiable (for instance using a telescoping apparatus).

The inventive temperature sensor may also preferably be used in a flat electrode that can be detachably attached to a living body, especially a counterelectrode for thermal surgery. For instance, the temperature sensor may be attached, especially glued, to an electrically insulated side or the back of the flat electrode. To reduce production costs, the temperature sensor may also be applied directly to one side of the electrode using vapor deposition.

The invention shall be explained in greater detail in the following using the enclosed drawings.

Identical components or components that have the same effect are identified with the same reference numbers in the figures.

Figure 1:
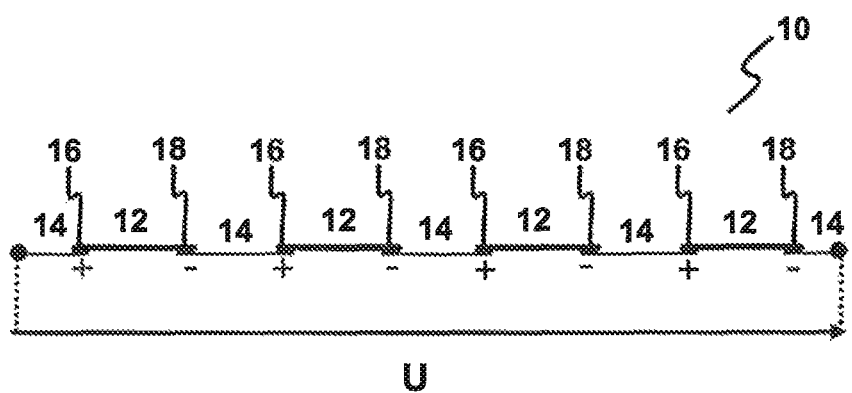
FIG. 1 is a schematic depiction of a series circuit of thermoelements.

A fundamental principle for the present invention is explained using the series circuit in the exemplary embodiment in FIG. 1, the series circuit being identified generally with 10. The series circuit 10 comprises an alternating electrical series circuit of first electrical conductors 12 and second electrical conductors 14. The electrical conductors 12 and 14 are different metals, alloys, or semiconductors. Thermojunctions are formed at the connection sites between the conductors 12 and 14, i.e., at the conductor junctions 16 and 18.

When there is an increase in temperature, the thermojunctions 16 supply a positive change in voltage, while when there is an increase in temperature the thermojunctions 18 supply a negative change in voltage. If all of the thermojunctions 16 and 18 have the same temperature, the measured voltage U equals zero. If the temperature at one of the thermojunctions 16 increases, the voltage U becomes positive, while a negative change in voltage U occurs if there is a point temperature increase at one of the thermojunctions 18. Even if there is only a point temperature change, the circuit 10 supplies a clearly detectable voltage response, i.e. a voltage U with full amplitude. This is because increases in temperature that occur only at one point are not suppressed by a mean value being formed.

Figure 2:
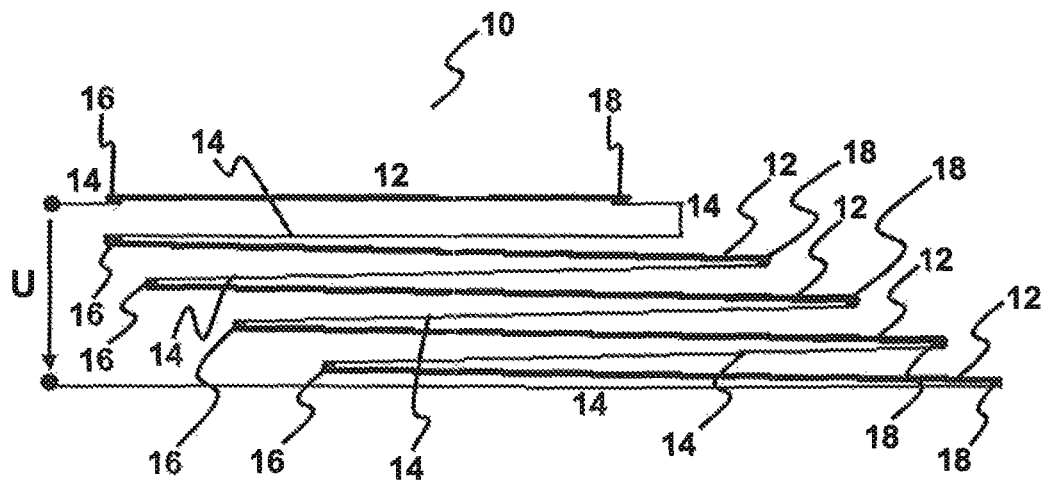
FIG. 2 is a schematic depiction of a first exemplary embodiment of an inventive temperature sensor.

FIG. 2 is a schematic depiction of a first exemplary embodiment of an inventive temperature sensor. The series circuit 10 in FIG. 2 is distinguished from the series circuit 10 in FIG. 1 in that the thermojunctions 16 and 18 are divided into two groups that are spatially separated from one another. The thermojunctions 16 are arranged grouped to the left and the thermojunctions 18 are arranged grouped to the right along two parallel straight lines. The depicted arrangement is only an example, however. The thermojunctions 16 and 18 may also be arranged along parallel circles, parallel circular arcs, parallel spirals, or parallel spiral arcs, for instance.

It is possible to roughly localize the area of the increase in temperature with the arrangement depicted in FIG. 2. Such a rough localization is sufficient for many fields of application for the inventive temperature sensor since frequently the user simply receives a signal about whether there is an increase in temperature. When using the inventive temperature sensor in an esophageal sensor, the user will frequently simply obtain the information that there has been an undesired overheating of tissue, whereupon the user can terminate the thermal surgical treatment.

The series circuit 10 in FIG. 2 may also be attached on one side of a flat counterelectrode for thermal surgery (not shown). To avoid skin carbonization, the series circuit 10 can detect whether the counterelectrode has detached from the skin. If, as shown in FIG. 2, the series circuit 10 is attached to one side of a counterelectrode, a positive increase in voltage signals the user of the counterelectrode that there has been an increase in temperature in the left-hand area of the counterelectrode. Similarly, when there is a negative increase in voltage, the user is signaled that there has been an increase in temperature in the right-hand area of the counterelectrode. Consequently the right-hand area of the counterelectrode has detached from the skin when there is a positive change in voltage U in the right-hand area and the left-hand area of the counterelectrode has detached from the skin when there is a negative change in voltage U.

Figure 3:
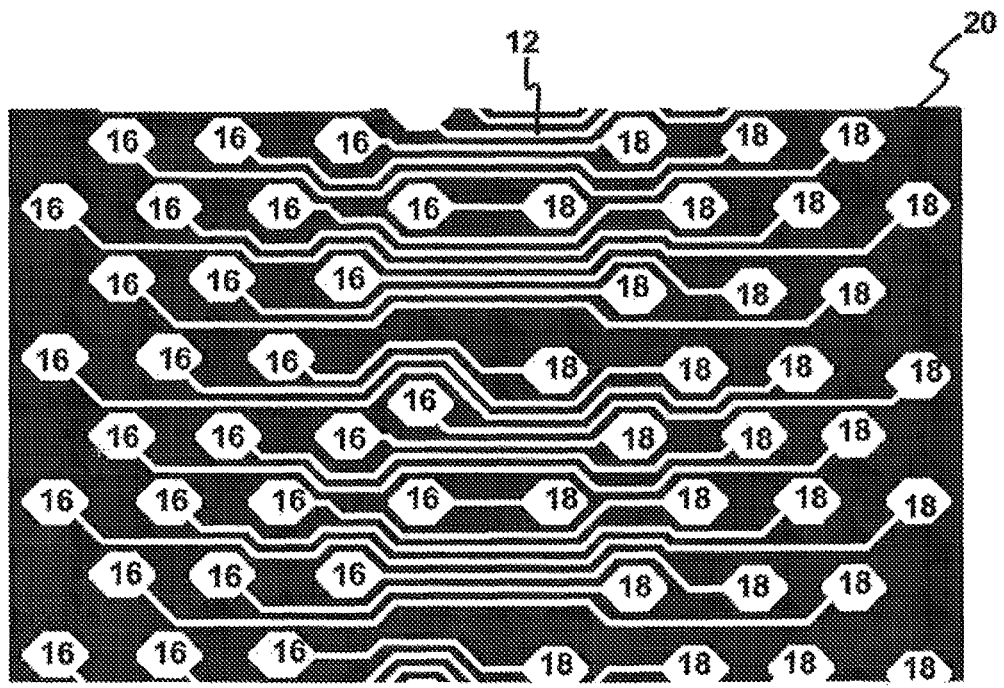
FIG. 3 is a schematic depiction of a first conductor structure of a second exemplary embodiment of an inventive temperature sensor.
Figure 4:
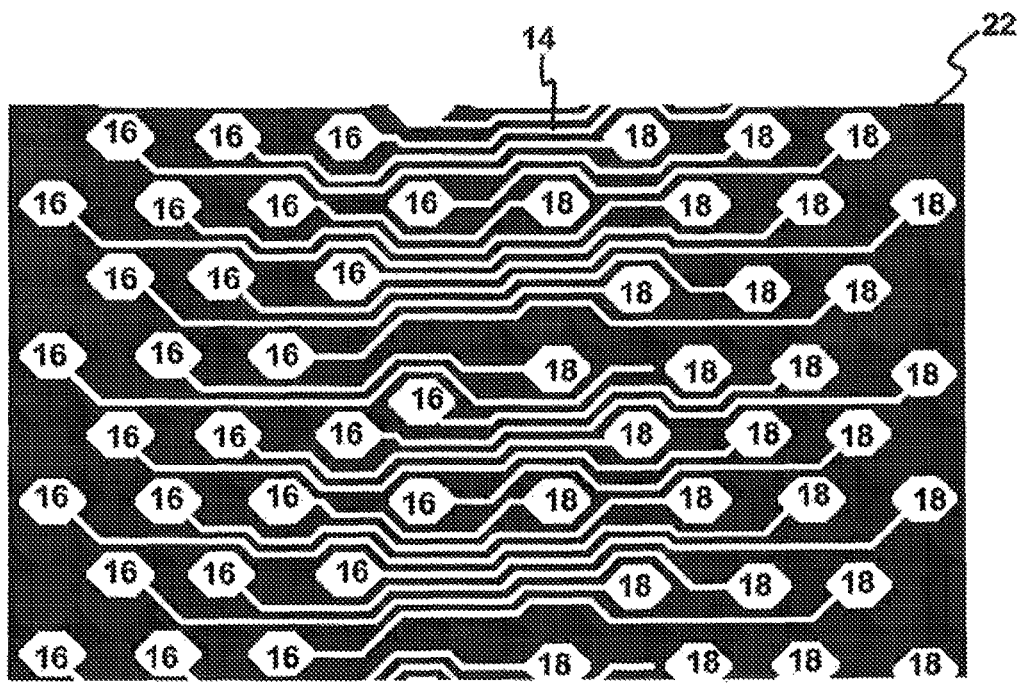
FIG. 4 is a schematic depiction of a second conductor structure of the second exemplary embodiment.
Figure 5:
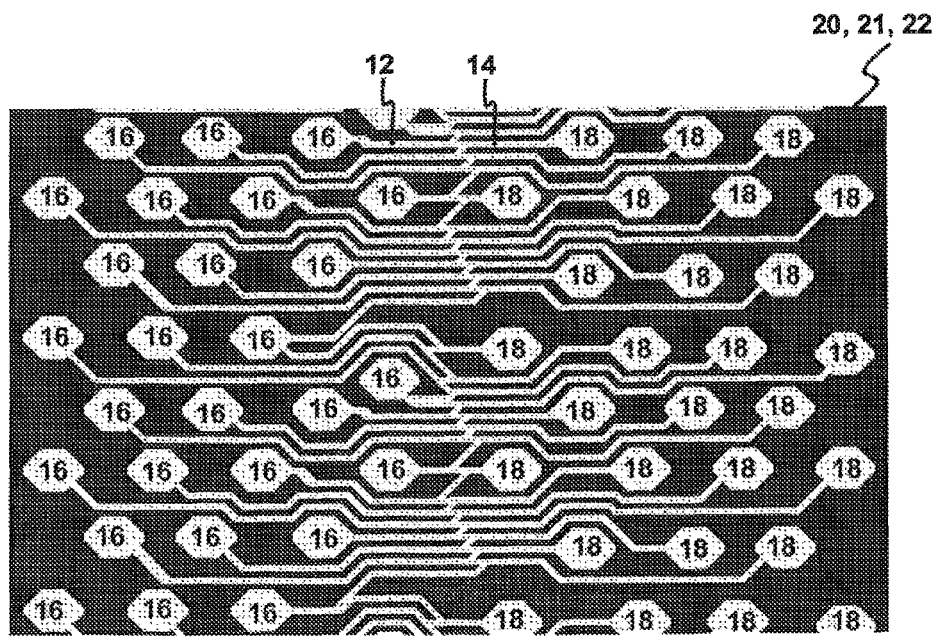
FIG. 5 is a schematic depiction of an overlaying of the first and second conductor structures from FIGS. 3 and 4.
Figure 6:
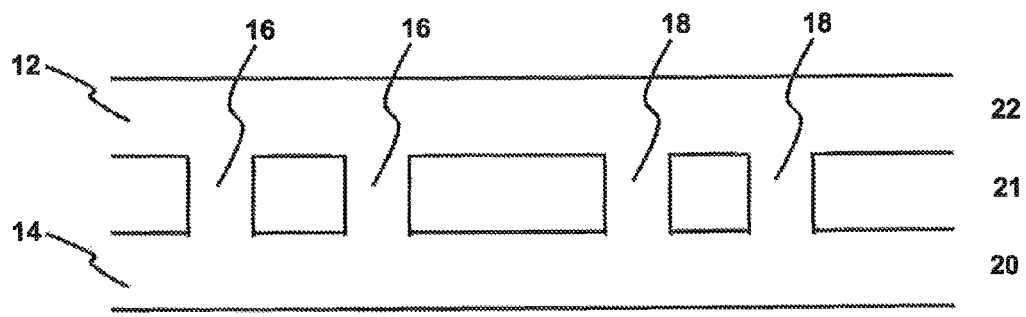
FIG. 6 is a schematic depiction of the inventive temperature sensor in accordance with the second exemplary embodiment.

FIGS. 3 through 6 are schematic depictions of a second exemplary embodiment of an inventive temperature sensor. FIG. 3 depicts a first conductor structure arranged in a first plane, FIG. 4 depicts a second conductor structure arranged in a second plane, FIG. 5 depicts the first and second conductor structures arranged above one another, and FIG. 6 depicts a side cross-sectional view of the first and second conductors.

As can be seen from FIG. 3, the first electrical conductor structure is arranged in the first plane 20. Each thermojunction area 16 is connected to a thermojunction area 18 via an electrical conductor track 12. The conductor tracks 12 are not arranged overlapping in the first plane 20. The conductor tracks 12 are embodied thin in order to provide space for as many thermojunction areas 16 and 18 as possible. In contrast, the thermojunction areas 16 and 18 have a flat, hexagonal shape in order to be able to be electrically connected in a simple manner to thermojunction areas 16 and 18 disposed in another plane. The hexagonal thermojunction areas 16 and 18 are depicted only as an example. Other shapes are possible, especially flat shapes. All of the electrical conductors 12 and thermojunction areas 16 and 18 depicted in FIG. 3 comprise the same metal.

FIG. 4 depicts the second conductor track structure arranged in the second plane 22. As in FIG. 3, each thermojunction area 16 is connected to a thermojunction area 18 via an electrical conductor track 14, all electrical conductors 14 and thermojunctions 16 and 18 comprising a metal that is different from the metal arranged in the first plane 20.

The conductor track structures arranged above one another, i.e. the layer structure from FIGS. 3 and 4, can be seen in FIGS. 5 and 6. The thermojunction areas 16 and 18 for the first plane 20 and those for the second plane 22 are arranged congruently above one another and have the same shape, thermojunctions between the first electrical conductors 12 and the second electrical conductors 14 being formed in the thermojunction areas 16 and 18. The first electrical conductors 12 and the second electrical conductors 14, that is, the thermojunction areas 16 and 18, are arranged such that they are electrically in series.

In addition, an electrically insulating layer 21 is arranged between the first plane 20 and the second plane 22. There are openings in the electrically insulating layer 21 in the thermojunction areas 16 and 18 in order to make possible the thermojunctions between the first electrical conductors 12 and the second electrical conductors 14. Using the electrically insulating layer 21, the first electrical conductors 12 and the second electrical conductors 14 may be arranged overlapping so that as many thermojunctions as possible are placed on the measurement surface. In particular the thermojunction areas 16 and 18 are distributed manner on a measurement surface of the sensor and electrically connected to form at least one series circuit, wherein thermojunctions formed by the thermocouples in each series circuit are divided between at least and preferably a total of two spatially separate groups such that in each group when there is a change in temperature the thermojunctions cause an equivalent change in voltage as homogeneously as possible in the planes 20 and 22. This makes it possible to detect with high probability point increases in temperature. Arranging the different conductors 12 and 14 in the two layers 20 and 22 makes it possible in a simple manner to distribute the thermojunctions 16 and 18 in two spatially separated groups, i.e. the grouping of the thermojunctions 16 to the left and of the thermojunctions 18 to the right in FIGS. 3 through 6.

In the following the manufacture of the three-dimensional layer structure depicted schematically in FIGS. 5 and 6 using an optical lithography method shall be described. However, other manufacturing methods are also possible.

The method essentially comprises successive three production steps in which the first metal structure 12, 16, 18 is added in the first plane 20 (see FIG. 3), the electrically insulating layer 21 is added (see FIG. 6), and the second metal structure 14, 16 18 is added in the second plane 22 (see FIG. 5).

For producing the first metal structure 12, 16, 18 depicted in FIG. 3, a mask arranged over a thin layer of film coating is exposed. The mask has the structure of the areas in black in FIG. 3. Then the film coating layer is developed, so the exposed areas 12, 16, 18 in the film coating layer are removed. Because of this, only the areas shown in black in FIG. 3 remain. Then the first metal layer is deposited. After that, the remaining film coating layer is removed so that the first metal structure 12, 16, 18 is obtained (as shown in white in FIG. 3).

In the next production step, the electrically insulating layer 21 is applied to the first metal structure 12, 16, 18 shown in FIG. 3. Then openings are formed in the electrically insulating layer 21 on the thermojunction areas 16 and 18. The openings can be etched into the electrically insulating layer 21, for instance, or formed with an optical lithography method.

Then the second metal structure 14, 16, 18, shown in FIG. 4, is applied to the electrically insulating layer 21. This may also be accomplished with the optical lithography method, as used for producing the first metal structure 12, 16, 18 depicted in FIG. 3. Another mask that has the structure of the area shown in black in FIG. 4 is used for this. When applying or depositing the second metal layer 14, 16, 18 on the electrically insulating layer 21, the second metal comes into contact with the first metal through the openings formed in the electrically insulating layer 21. This forms the thermojunctions 16 and 18.

Consequently, using the aforesaid manufacturing method a metal layer structure is provided in which different metal layers are arranged essentially in two parallel planes 20 and 22, and there are electrical connections between the different metal layers essentially in planes that are perpendicular to the parallel planes 20 and 22. Thus a series circuit of alternating first electrical conductors 12 and second electrical conductors 14 can be created with a relatively uncomplicated production method.

It is also possible for a plurality of layer structures 20, 21, 22 to be disposed over one another so that a plurality of thermojunctions 16, 18 that are connected in electrical series are arranged above one another in different planes. In particular for more precise localization of an increase in temperature at least one thermojunction from one series circuit may be arranged between at least two thermojunctions connected in a different electrical series. Similarly, increasing the number of series circuits arranged above one another can improve the accuracy of the localization of increases in temperature.

Figure 7:
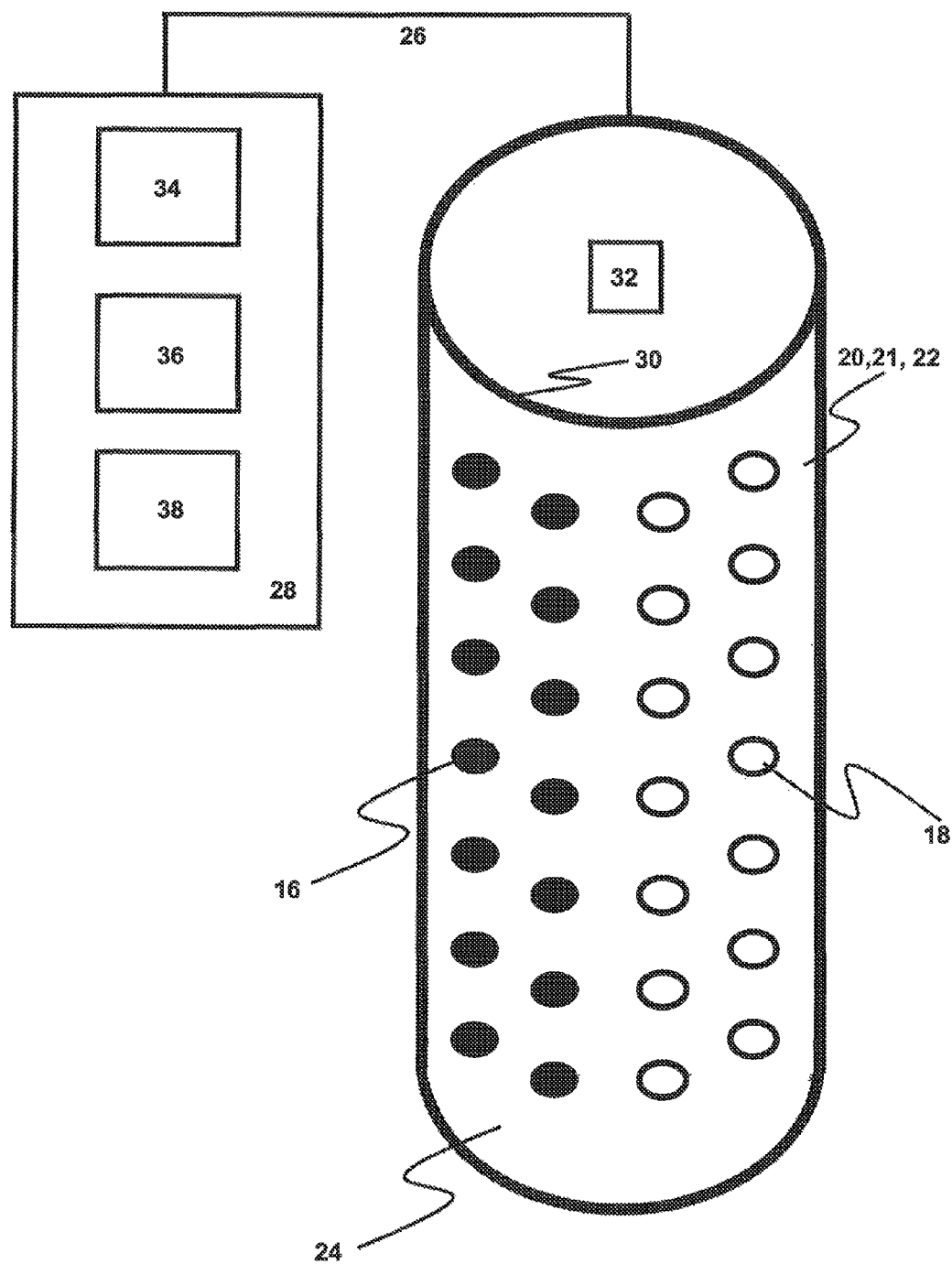
FIG. 7 is a schematic depiction of a first exemplary embodiment of an inventive esophageal sensor.

FIG. 7 is a schematic depiction of a first exemplary embodiment of an inventive esophageal sensor 24. The esophageal sensor 24 is connected to an evaluation unit 28 via a line 26. The line 26 is a cable via which the esophageal sensor 24 can be inserted into and withdrawn from the esophagus.

The esophageal sensor 24 has a flat body 30 that forms the measurement surface of the esophageal sensor 24. The flat body 30 has a circular cylinder shape and comprises plastic. However, the shape of the present invention is not limited to a circular cylinder or and the material is not limited to plastic. Other shapes, especially longitudinal shapes, and other metals are possible. The temperature sensor 16, 18, 20, 21, 22 depicted in FIGS. 5 and 6 is bent and glued to the flat body 30.

In addition to the thermojunctions 16 and 18, the esophageal sensor 24 has a temperature sensor 32. The temperature sensor 32 measures the temperature and supplies measured temperature values to the evaluation unit 28. In addition, voltage change measured values from the temperature sensor 16, 18, 20, 21, 22 are fed to the evaluation unit 28.

The evaluation unit 28 has an electrical switch 34, a temperature display 36, and a warning apparatus 38. The electrical circuit 34 forms absolute values for the voltage change measured values and adds them to the measured temperature values from the temperature sensor 32. The values determined by the electrical circuit 34 are fed to the display apparatus 36 and displayed by the latter. The warning apparatus 38 outputs a warning signal if certain values from the electrical circuit 34 exceed a pre-specified limit. It is also possible for the evaluation unit to be connected to a thermal surgery apparatus (not shown) and for the thermal surgery apparatus to turn off automatically when an increase in temperature exceeds a limit. This can prevent undesired overheating of tissue.

Figure 8:
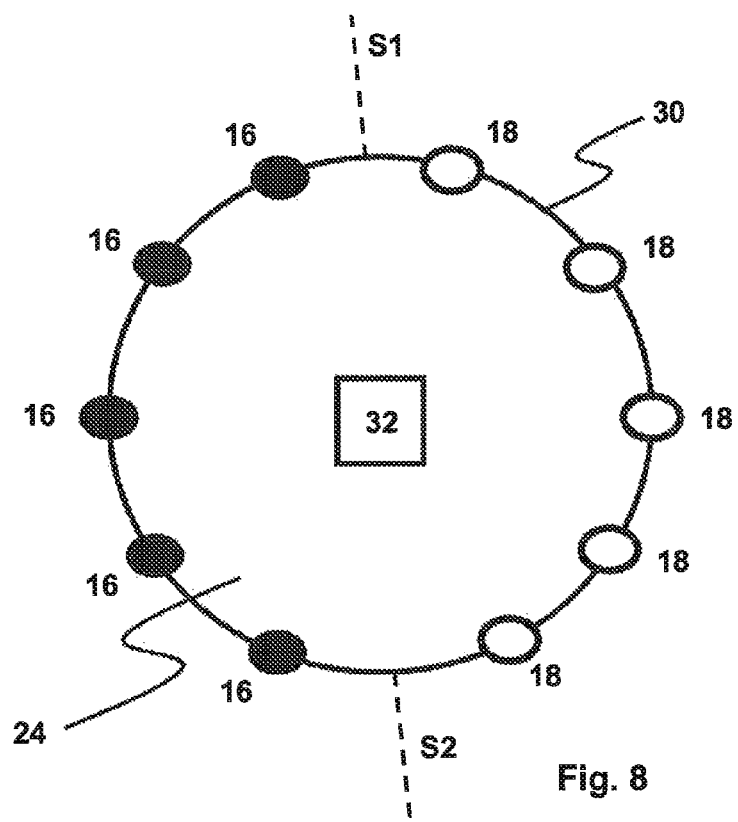
FIG. 8 is a schematic view from above of the esophageal sensor from FIG. 7; and, FIG. 9 is a schematic depiction of a second exemplary embodiment of an inventive esophageal sensor.

FIG. 8 is a schematic depiction of a view of the esophageal sensor 24 in FIG. 7 from above. As can be seen from FIG. 8, using a grouped arrangement or division of the thermojunctions 16 and 18 it is possible to detect the half of the esophageal sensor 24 in which a change in temperature occurs. To this end the esophageal sensor 24 may be moved into a desired orientation, for instance by rotating the cable 26 using an endoscope (not shown).

However, there can be problems if a point (i.e. small surface area) increase in temperature occurs in either of the areas S1 or S2, i.e. in an area between the thermojunction groups 16 and 18. In this case the changes in voltage produced by the thermojunctions 16 and 18 may be raised to zero, which means that an increase in temperature cannot be detected.

Figure 9:
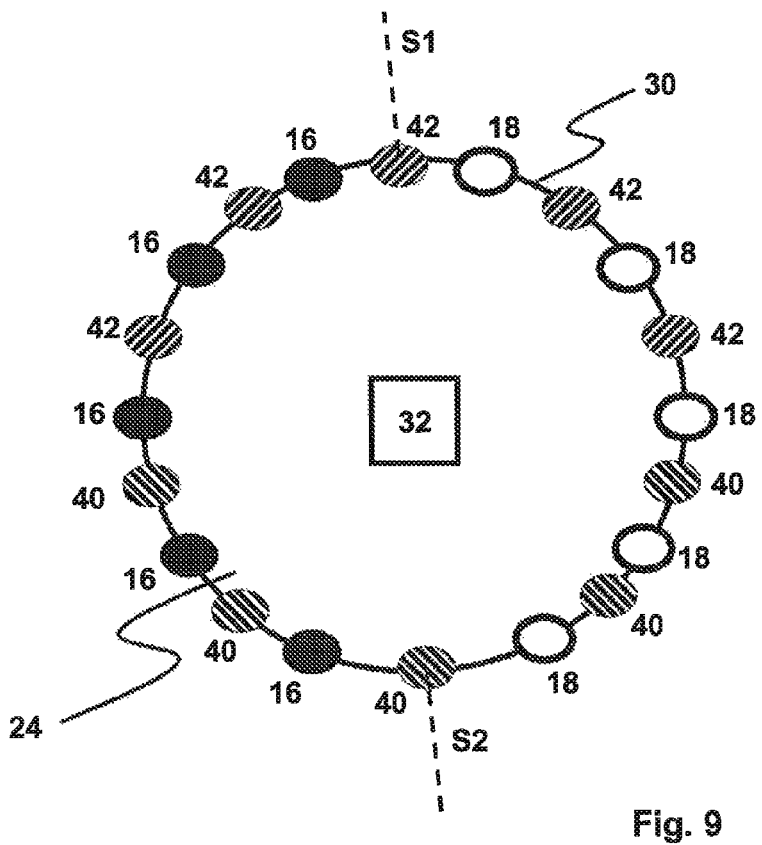

A second series circuit of thermocouples to solve this problem may be provided. FIG. 9 is a schematic depiction of a view from above of a second exemplary embodiment of an esophageal sensor 24 having two series circuits of thermocouples.

The exemplary embodiment in FIG. 9 is distinguished from the exemplary embodiment in FIGS. 7 and 8 in that thermojunctions 40 and 42 of a second series circuit are arranged between the thermojunctions 16 and 18 of the first series circuit. When there is an increase in temperature, the thermojunctions 40 supply a positive change in voltage, while the thermojunctions 42 supply a negative change in voltage when there is an increase in temperature. As may be seen from FIG. 9, the thermojunctions 16 and 18 that are directly adjacent with the shortest distance to one another are offset by 90° to the thermojunctions 40 and 42 that are directly adjacent with the shortest distance to one another on the measurement surface 30 of the esophageal sensor 24. This arrangement of the thermojunctions 16, 18, 40, 42 defines four measurement areas. Thus it is possible to establish in which of the four measurement areas an increase in temperature occurs. By increasing the number of series circuits it is possible to increase the number of measurement areas so that even more precise localization of increases in temperature is possible. For instance, if three series circuits are arranged above one another, the thermojunctions directly adjacent with the shortest distance to one another may be offset to one another by 60° on the measured surface so that increases in temperature can be localized in six measurement areas.

If there is a point temperature increase in one of the areas S1 or S2, this increase in temperature is detected by the thermojunction 40 or 42 from the second series circuit that is arranged in the areas S1 or S2, so that the point temperature increase can be reliably detected, even when there are mutually offsetting changes in voltage for the thermojunctions 16 and 18 from the first series circuits.

The arrangements of the thermojunctions 16 and 18 on the measured surface as depicted in FIGS. 1 through 8 are only examples. A plurality of different arrangements is possible. Thus, for instance, with the esophageal sensors 24 depicted in FIGS. 7 through 9 it is possible for a group of thermojunctions 16 to be arranged in the center of the circular cylinder 30 (i.e. with the temperature sensor 32), the thermojunctions 18 of the other group being disposed on the surface of the circular cylinder 30.

Moreover, the exemplary embodiments provided in the foregoing related only to undesired overheating of tissue (i.e. increases in temperature) in thermal surgery. However, the present invention may also be employed in a cold therapy, especially in so-called "cryotechnology," i.e. ablation of living tissue using cold. Correspondingly, the inventive temperature sensor may detect an undesired reduction in the temperature of living tissue.

The invention claimed is:

1. A temperature sensor for measuring the temperature in a living body, the temperature sensor comprising:
   a flexible circuit board having a first layer and a second layer,
   wherein the first layer has a plurality of first conductors disposed therein, and
   wherein the second layer has a plurality of second conductors disposed therein, the plurality of second conductors being of a different material than the plurality of first conductors, wherein the first and second electrical conductors form a plurality of thermocouples electrically connected to create at least a first series circuit;
   wherein thermojunctions formed by the thermocouples in the first series circuit are divided into first and second spatially separate groups such that in each of the first and second groups when there is a change in temperature the thermojunctions cause an equi-directional change in voltage,
   wherein the first and second layers are arranged to form a cylindrical measurement surface of the sensor, and
   wherein the first and second groups of thermojunctions are arranged in different circumferential sections of the cylindrical measurement surface.

2. The temperature sensor in accordance with claim 1 wherein the thermojunctions of each of the first and second groups are arranged in rows and columns.

3. The temperature sensor in accordance with claim 1, wherein the first electrical conductors are disposed with no mutual overlap in the first layer and the second electrical conductors are disposed with no mutual overlap in the second layer.

4. The temperature sensor in accordance with claim 3, wherein some of the first electrical conductors disposed in the first layer and some of the second electrical conductors disposed in the second layer overlap one another.

5. The temperature sensor in accordance with claim 1, wherein the thermocouples are electrically connected to create a second series circuit in addition to the first series circuits,
   wherein thermojunctions formed by the thermocouples in the second series circuit are divided into third and fourth spatially separate groups such that in each of the third and fourth groups when there is a change in temperature the thermojunctions cause an equi-directional change in voltage,
   wherein the third and fourth groups of thermojunctions are arranged in different circumferential sections of the cylindrical measurement surface at an angular offset with respect to the first and second groups.

6. The temperature sensor in accordance with claim 5 wherein the angular off-set is about 90 degrees.

7. The temperature sensor in accordance with claim 1, including:
   an electrical circuit configured to determine an absolute value of a measured value from the temperature sensor.

8. The temperature sensor in accordance with claim 7, including:
   a temperature probe for measuring a temperature value,
   wherein the electrical circuit is configured to add the temperature value measured by the temperature probe and the determined absolute value.

9. The temperature sensor in accordance with claim 1, wherein the first series circuit includes a plurality of thermojunctions that extend between the first layer and the second layer wherein the electrical path formed by the at least one series circuit alternates between the first and second layers at each thermo junction of the plurality of thermojunctions.

10. The temperature sensor in accordance with claim 1 wherein the first and second groups of thermojunctions are distributed across diametrically opposed surface postions of the cylindrical measurement surface.

11. A method of measuring a temperature in an esophagus, the method comprising:
    Providing a flexible circuit board adapted as a temperature sensor, and electronic evaluation unit and a connection line for connection of the temperature sensor with the electronic evaluation unit, the flexible circuit board comprising:
       a first layer having a plurality of first conductors disposed therein;
       a second layer having a plurality fo second conductors disposed therein, the plurality of second conductors being of a different material than the plurality of first conductors, wherein the plurality of first conductors and the plurality of second conductors form a plurality of thermocouples electrically connected to create at least a first series circuit,
    wherein thermojunctions formed by the plurality of thermocouples in the first series circuit are divided into first and second spatially separate groups such that in each of the first and second groups when there is a change in temperature the thermojunctions cause an equi-directional change in voltage,
    wherein the first layer and the second layer are arranged to form a cylindrical measurement surface of the sensor, and
    wherein the first and second groups of thermojunctions are arranged in different circumferential sections of the cylindrical measurement surface;
    inserting the temperature sensor into an esophagus; and
    using the evaluation unit to evaluate a measured value received from the temperature sensor by way of the connection line.

* * * * *